United States Patent
Golub et al.

(10) Patent No.: US 6,277,061 B1
(45) Date of Patent: *Aug. 21, 2001

(54) METHOD OF INHIBITING MEMBRANE-TYPE MATRIX METALLOPROTEINASE

(75) Inventors: Lorne M. Golub, Smithtown; Hsi-Ming Lee, Setauket, both of NY (US); Timo Sorsa; Olli Teronen, both of Helsinki (FI); Tuula Salo, Oulu (FI)

(73) Assignee: The Research Foundation of State University of New York, Albany, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/052,222

(22) Filed: Mar. 31, 1998

(51) Int. Cl.[7] ................................................. A61K 31/65

(52) U.S. Cl. ................................................. 517/152

(58) Field of Search ............................................. 514/152

(56) References Cited

U.S. PATENT DOCUMENTS 5,837,696    11/1998   Golub et al. .................... 514/152

FOREIGN PATENT DOCUMENTS

WO 92/12717   8/1992   (WO).
WO 98/04287   2/1998   (WO).

OTHER PUBLICATIONS

Imai K, Ohuchi E, Aoki T, Nomura H, Fujii Y, Sato H, Seiki M and Okada Y, *Cancer Res* 56:2702–2710 (1996).
Pei D and Weiss SJ, *Nature* 371: 244–247 (1994).
Yu AE, Hewitt RE, Connor EW, Stetler–Stevenson WG, "Matrix metalloproteinases, Novel targets for directed cancer therapy," *Drugs Aging* 11(3):229–244 (1997).
Lee HM, Cao C, Zucker S, Sorsa T, Golub, LM, "CMT–3, a Modified Non–Antimicrobial Tetracycline, Inhibits MT1–MMP Mediated Gelatinolysis and Pro–MMP–2 Activation: Relevance to Cancer," *Journal of Dental Research* vol. 77, special issue B, abstract #926 (1998).
Cao J, Rehemtulla A, Bahou W, and Zucker S, "Membrane type matrix metalloproteinase 1 activates pro–gelatinase A without furin cleavage of the N–terminal domain," *J Biol Chem* 271:30174–30180 (1996).
Cao J, Lee HM, Bahou W, and Zucker S, "The propeptide domain of membrane type 1–matrix metalloproteinase (MT1–MMP) is required for progelatinase A activation and binding of TIMP–2," *AACR Annual Meeting*, Mar. 28–Apr. 1, New Orleans, LA (1998).
DeClerck YA, Shimada H, Taylor SM, and Langley KE, "Matrix metalloproteinases and their inhibitors in tumor progression," *Annals NY Acad Sci* 732:222–232 (1994).

Fridman R, Toth M, Pena D, and Mobashery S, "Activation of progelatinase B (MMP–9) by gelatinase A (MMP–2)," *Cancer Res* 55:2548–2555 (1995).
Golub LM, Ramamurthy NS, McNamara TF, Greenwald RA, and Rifkin BR, "Tetracyclines inhibit connective tissue breakdown: New therapeutic implications for an old family of drugs," *Crit Rev Oral Biol Med* 2(2):297–322 (1991).
Golub LM, Sorsa T, and Suomalainen K, *Curr Opin Dent* 2:80–90 (1992).
Kroon AM, Dontje BHJ, Holtrop M, and van den Bogert C, "The mitochondrial genetic system as a target for chemotherapy: tetracyclines as cytostatics," *Cancer Letts* 25(1):33–40 (1984).
Lee AY, Akers KT, Collier M, Li T, Eisen AZ, and Seltzer JL, "Intracellular activation of gelatinase A (72–kDa type IV collagenase) by normal fibroblasts," *Proc Natl Acad Sci USA* 94(9):4424–4429 (1997).
Lichte A, Kolkenbrock H, and Tschesche H, "The recombinant catalytic domain of membrane–type matrix metalloproteinase–1 ($MT_1$–MMP) induces activation of progelatinase A and progelatinase A complexed with TIMP–2," *FEBS Lett* 397:277–287 (1996).
Lokeshwar BL, Selzer MG, Block NL, and Gunja–Smith Z, "Secretion of matrix metalloproteinases and the inhibitors (TIMPs) by human prostate in explant cultures: Reduced tissue inhibitor of metalloproteinase secretion by malignant tissues," *Cancer Res* 53:4493–4498 (1993).
Maragoudakis ME, Peristeris P, Missirlis E, Aletras A, Andriopoulou P, and Haralabopoulos G, *Annals NY Acad Sci* 732:280–293 (1994).
Mitscher LA, *The Chemistry of the Tetracycline Antibiotics*, Ch. 6, Marcel Dekker, New York (1978).
Murphy G, Willenbrock F, Ward RV, Cockett MI, Eaton D, and Docherty AJ, *Biochem J* 283:637–641 (1992).
Nagase H, "Matrix metalloproteinases," Chapter 7, pp. 153–204, in *Zinc Metalloproteinases in Health and Disease*, Hooper NM, ed., Taylor and Francis, London (1996).
Ohuchi E, Imai K, Fujii Y, Sato H, Seiki M, and Okada Y, "Membrane type 1 matrix metalloproteinase digests interstitial collagens and other extracellular matrix macromolecules," *J Biol Chem* 272(4):2446–2451 (1997).

(List continued on next page.)

*Primary Examiner*—Jerome D. Goldberg
(74) *Attorney, Agent, or Firm*—Hoffmann & Baron, LLP

(57) ABSTRACT

The invention is a method of inhibiting the activity of membrane-type matrix metalloproteinase (MT-MMP) in biological systems. Accordingly, the invention permits the treatment of medical conditions in mammals that are characterized by MT-MMP activity, and especially those conditions characterized by excessive MT-MMP activity. The method employs a tetracycline compound, preferably a non-antimicrobial tetracycline, and more preferably 6-demethyl-6-deoxy-4-de(dimethylamino)tetracycline (CMT-3) or 6-α-deoxy-5-hydroxy-4-de(dimethylamino) tetracycline (CMT-8) to inhibit the MT-MMP activity.

7 Claims, 7 Drawing Sheets

OTHER PUBLICATIONS

Okada Y, Bellocq J–P, Rouyer N, Chenard M–P, Rio M–C, Chambon P, and Basset P, "Membrane–type matrix metalloproteinase (MT–MMP) gene is expressed in stromal cells of human colon, breast, and head and neck carcinomas," *Proc Natl Acad Sci USA* 92:2730–2734 (1995).

Sato H, Takino T, Okada Y, Cao J, Shinigawa A, Yamamoto E, and Seiki M, "A matrix metalloproteinase expressed on the surface of invasive tumour cells," *Nature* 370:61–65 (1994).

Sato H, Kinoshita T, Takino T, Nakayama K, and Seiki M, "Activation of a recombinant membrane type 1– matrix metalloproteinase (MT1–MMP) by furin and its interaction with tissue inhibitor of metalloproteinases (TIMP)–2," *FEBS Lett* 393:101–104 (1996).

Sato T, del Carmen Ovejero M, Hou P, Heegaard AM, Kumegawa M, Foged NT, and Delaisse JM, "Identification of the membrane–type matrix metalloproteinase $MT_1$–MMP in osteoclasts," *J Cell Science* 110:589–596 (1997).

Seftor REB, Seftor EA, DeLarco JE, Kleiner DE, Leferson J, Stetler–Stevenson WG, McNamara TF, Golub LM, and Hendrix MJC, "Chemically–modified tetracyclines inhibit human melanoma cell invasion and metastasis," *Clin Exp Metastasis* 16 (In Press). No Date.

Shofuda K, Yasumitsu H, Nishihashi A, Miki K, and Miyazaki K, "Expression of three membrane–type matrix metalloproteinases (MT–MMPs) in rat vascular smooth muscle cells and characterization of MT3–MMPs with and without transmembrane domain," *J Biol Chem* 272(15)9749–9754 (1997).

Strongin AY, Collier I, Bannikov G, Marmer BL, Grant GA, and Goldberg GI, "Mechanism of cell surface activation of 72 kDa Type IV collagenase: Isolation of the activated form of the membrane metalloproteinase," *J Biol Chem* 270(10):5331–5338 (1995).

Takino T, Sato H, Yamamoto E, and Seiki M, "Cloning of a human gene potentially encoding a novel matrix metalloproteinase having a C–terminal transmembrane domain," *Gene* 155:239–298 (1994).

Uitto VJ, Firth JD, Nip L, and Golub LM, *Annals NY Acad Sci* 732:140–151 (1994).

van den Bogert C, Dontje BHJ, Holtrop M, Melis TE, Romijn JC, van Dongen JW, and Kroon AM, "Arrest of the proliferation of renal and prostate carcinomas of human origin by inhibition of mitochondrial protein synthesis," *Cancer Res* 46(7):3283–3289 (1986).

Zucker S, Lysick RM, Ramamurthy NS, Golub LM, Wieman JM, and Wilkie DP, "Diversity of plasma membrane proteinases in mouse melanoma cells: Inhibition of collagenolytic activity and cytolytic activity by minocycline," *J Natl Cancer Inst* 75:517–525 (1985).

Zucker S, Conner C, DiMassimo BI, Ende BI, Drews M, Seiki M, and Bahou WF, *J Biol Chem* 270:23730–23738 (1995).

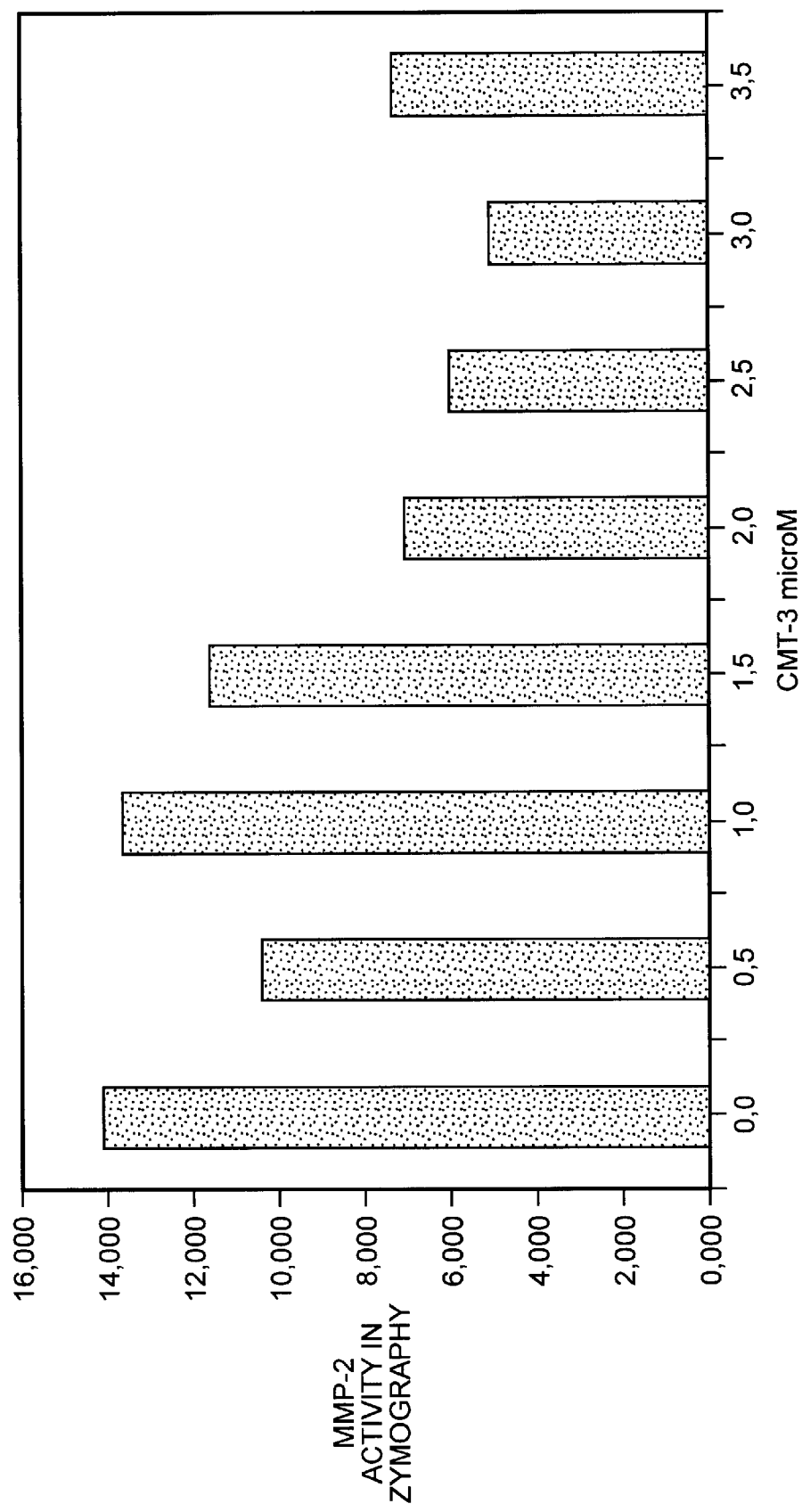
FIG. 4A  TOTAL MMP-2 PRODUCTION BY CON-A INDUCED MG-63 CELLS

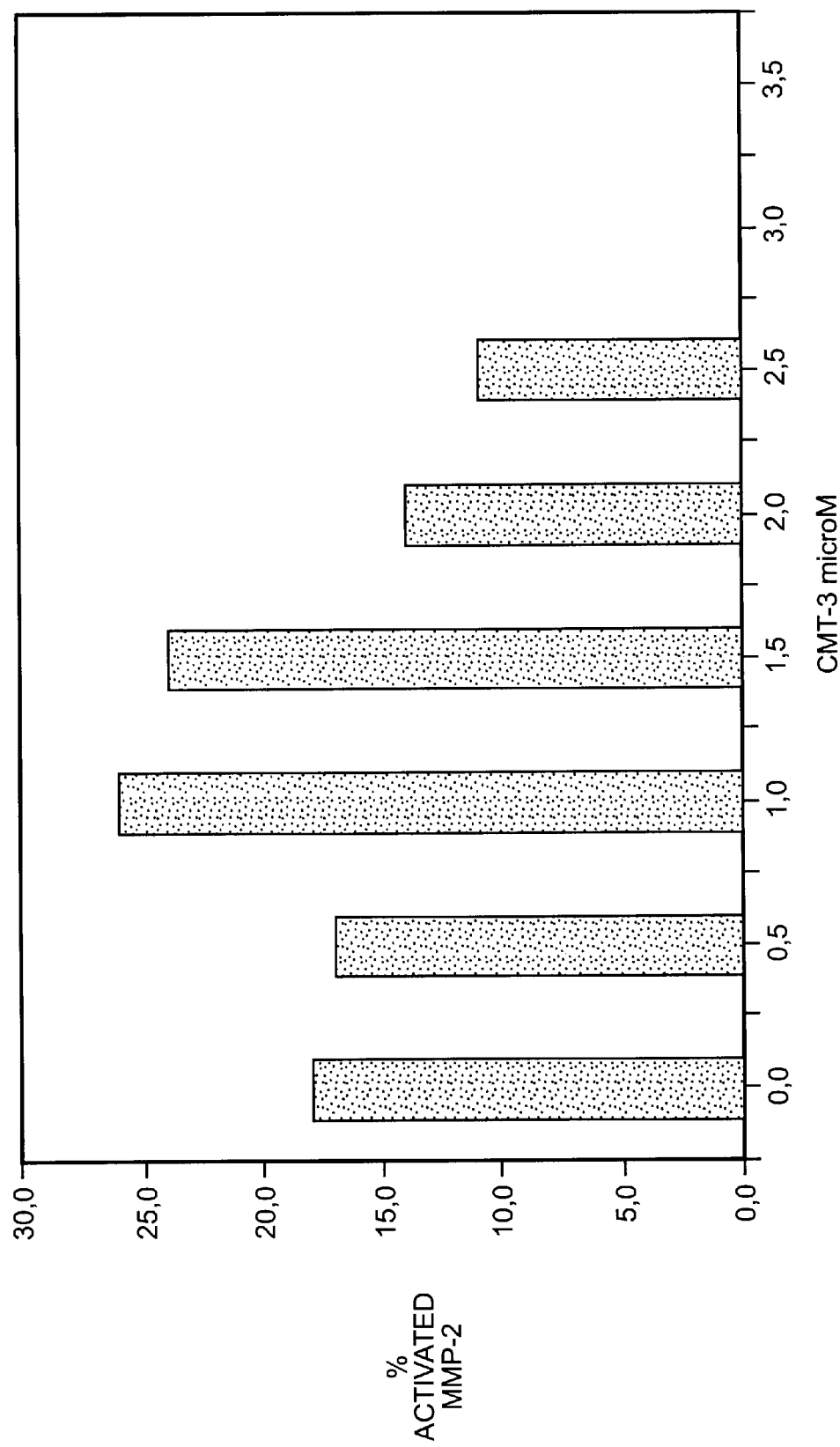
FIG. 4B ACTIVE MMP-2 IN CON-A INDUCED MG-63 CELL MEDIA

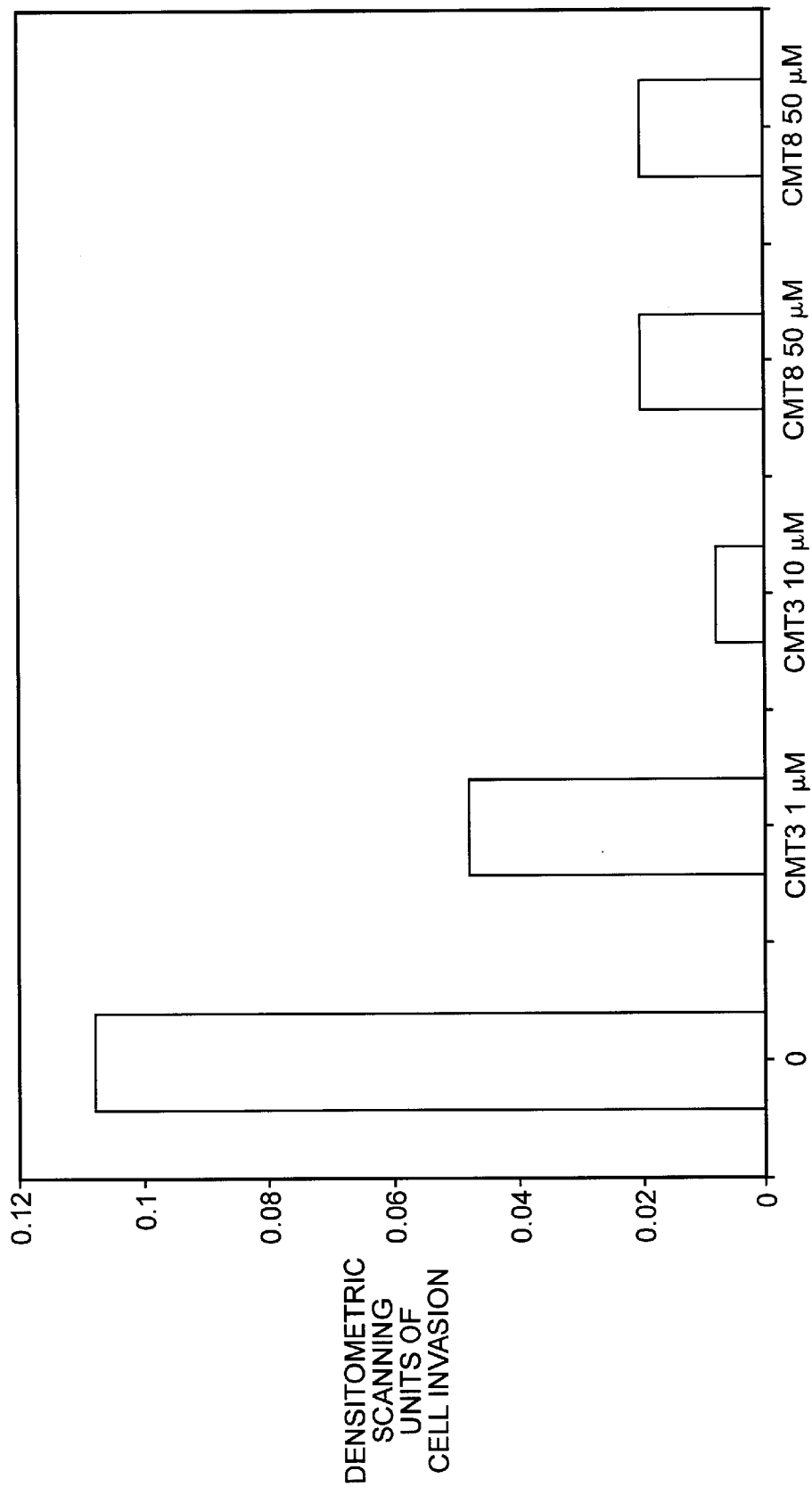
FIG. 5A  INHIBITION OF HT1080 FIBROSARCOMA CELL MATRIGEL-INVASION BY CMTs

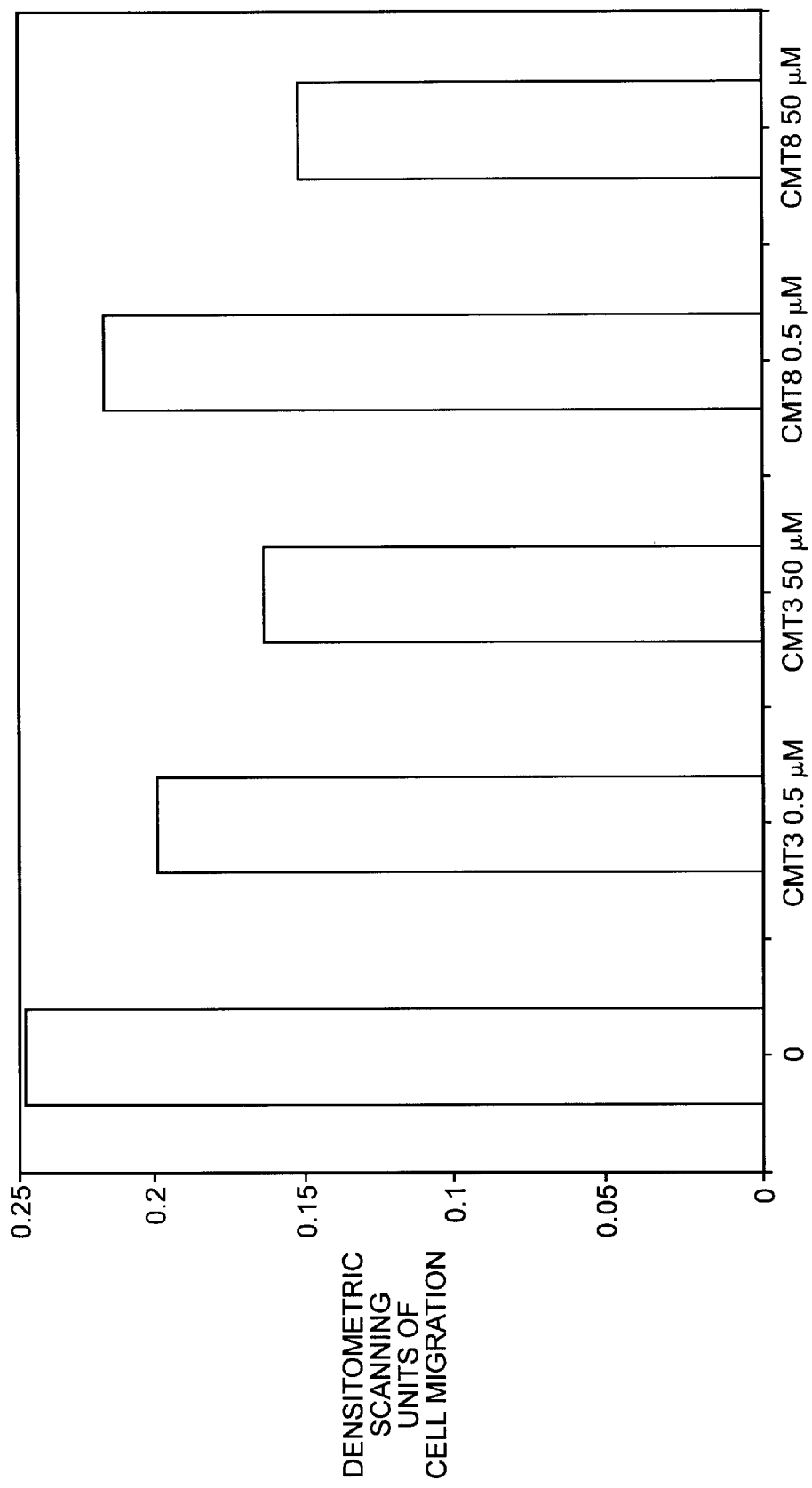

METHOD OF INHIBITING MEMBRANE-TYPE MATRIX METALLOPROTEINASE

This invention was made with Government support under Grant No. R37-DE03987 awarded by the National Institutes of Health through the National Institute of Dental Research. The Government has certain rights in the invention.

BACKGROUND OF THE INVENTION

The invention relates to methods of inhibiting the activity of membrane-type matrix metalloproteinase (MT-MMP) in biological systems. More specifically, the invention relates to the use of tetracycline compounds for the inhibition of MT-MMP in mammals.

Matrix metalloproteinases MMPs, matrixins) are a family of related proteolytic enzymes expressed by a wide variety of cells and tissue types in both normal and abnormal situations. These zinc-binding metalloendopeptidase enzymes are unified as a family by virtue of structural homologies, and by proteolytic activity against many components of the extracellular matrix (ECM). As a result, the MMPs play important roles in development and morphogenesis as well as in tissue remodeling following injury. In particular, matrix metalloproteinases are distinguished from other metalloproteinases by virtue of their susceptibility to activation of the zymogen by thiol-modifying reagents (e.g., 4-aminophenyl mercuric acetate (APMA) and other mercurial compounds, N-ethylmaleimide, oxidized glutathione), their inhibition by a group of endogenous substances known collectively as "tissue inhibitors of metalloproteinases" or "TIMPs," and the presence of a consensus sequence in the propeptide forms. Nagase (1996).

However, the MMPs have widely divergent substrate specificities and activities, leading to their classification into a series of subtypes. The collagenases include interstitial collagenase (MMP-1), neutrophil collagenase (MMP-8), and collagenase-3 (MMP-13), and are characterized by their ability to specifically degrade triple helical regions of collagens I, II, and II. The gelatinases include gelatinase A (MMP-2; 72-kDa gelatinase) and gelatinase B (MMP-9; 92-kDa gelatinase), and are characterized by their ability to specifically cleave gelatins, but they are further characterized by their ability to hydrolyze collagen IV, elastin and other substrates. The stromelysins include stromelysin 1 (MMP-3), stromelysin 2 (MMP-10), and in certain systems stromelysin 3 (MMP-1). The stromelysins 1 and 2 characteristically degrade a variety of substrates including aggrecan, fibronectin, laminin, numerous collagen types, and play a role in activation of other enzymes.

The MMP family also includes several other MMPs that do not neatly fit into the collagenase, gelatinase, and stromelysin subfamilies. Matrilysin (MMP-7; PUMP-1) differs substantially in structure, lacking a C-terminal domain common to the other MMPs. Metalloelastase (MMP-12) is characterized by its ability to degrade elastin.

A more recently discovered MMP that is substantially distinct from the conventional MMP structural subfamilies is membrane-type matrix metalloproteinase (MT-MMP). MT-MMP differs from other MMPs in a number of ways. For example, most MMPs are secreted by the cells in which they are made, but MT-MMP, as is implicit in its name, is expressed as a membrane-bound protein on the surface of the cell. It is believed that this feature is unique among the MMPs and that such expression may be attributable to a hydrophobic domain of up to 24 amino acids. See Nagase (1996).

The MT-MMP enzyme also has characteristic substrate specificity, with particular capacity for converting pro-MMP-2 and pro-MMP-9 into the active forms of these gelatinases (Murphy et al. 1992; Zucker et al. 1995). However, MT-MMP is also characterized by direct degradation of gelatin. MT-MMP may further act as a surface receptor for TIMP-2, and the resulting MT-MMP/TIMP-2 complex may then act as a receptor for pro-gelatinase A, which can activate the gelatinase (Strongin et al. 1995; Cao et al. 1996; Lichte et al. 1996). This plasma membrane-activated MMP-2 can in turn activate pro-MMP-9 and this process is inhibited by TIMPs (Fridman et al. 1995).

Unlike other MMPs, MT-MMPs and MMP-1 (stromelysin-3) are activated by an intracellular proteinase, furin, a Golgi-associated serine proteinase (Pei and Weiss 1995). Similar to MMP-11, the mechanism of activation of MT-MMP is under investigation and may also involve an intracellular activation through a sequence which can be recognized by furin-like enzymes (Sato et al. 1996). Recently, Cao et al. (1996) demonstrated that the 63 kDa pro-MT-MMP expressed on the cell surface has not been processed (contransfection with furin did not change the molecular weight of MT-MMP). These authors hypothesize that conformational effects induced by the plasma membrane localization of MT-MMP may provide functional activity to pro-MMP-2 without cleavage of the molecule. Receptor-bound TIMP-2 may participate in this process.

Investigators have identified MT-MMP expression by normal tissues, e.g., placenta, lung, and kidney (Takino et al. 1994). A form of MT-MMP, identified as membrane-type 1 MMP ($MT_1$-MMP) has also been found to be expressed by osteoclasts, the principal cell type involved in bone resorption (Sato et al 1997). Other investigators have identified three different forms of MT-MMP expressed by rat smooth muscle cells, that appear to be involved in matrix remodeling of blood vessels (Shofuda et al 1997).

Lee et al. (1997) have observed expression of a gelatinase activator that appears to localize to the Golgi membranes. Lee et al. hypothesize that this activator may be MT-MMP, and that a change in localization of this activator to the plasma membrane may occur in tumor cells. Other investigators have identified excessive MT-MMP expression by lung carcinomas (Sato et al. 1994). Still others have seen MT-MMP expression by fibroblasts in tumor stroma of colon, breast, head and neck carcinomas (Okada et al. 1995).

MT-MMP expressed on cancer cell membranes also is an extracellular matrix-degrading enzyme sharing the substrate specificity with interstitial collagenases (i.e., digestion of type I, II, and III collagens into characteristic ¾ and ¼ fragments) (Ohuchi et al. 1997; Cao et al. 1998). As noted above, MT-MMP also exhibits gelatinolytic activity, as measured by gelatin zymography (Imai et al. 1996). Thus, MT-MMP may play a dual role in pathophysiological digestion of extracellular matrix through direct cleavage of the substrates and activation of pro-MMP-2, which is produced constitutively in relatively high concentrations by many cell types including tumor cells (Sato et al. 1994; Sato et al. 1997).

Tetracycline and a number of its chemical relatives form a particularly successful class of antibiotics. Certain of the tetracycline compounds, including tetracycline itself, as well as sporocycline, etc., are broad spectrum antibiotics, having utility against a wide variety of bacteria. The parent compound, tetracycline, has the following general structure:

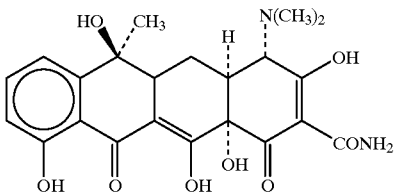

The numbering system for the multiple ring nucleus is as follows:

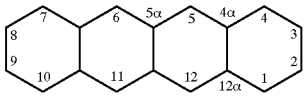

Tetracycline, as well as the 5—OH (terramycin) and 7—Cl (aureomycin) derivatives, exist in nature, and are all well known antibiotics. Semisynthetic derivatives such as 7-dimethylamino-tetracycline (minocycline) and 6α-deoxy-5-hydroxy-tetracycline (doxycycline) are also known antibiotics. Natural tetracyclines may be modified without losing their antibiotic properties, although certain elements of the structure must be retained to do so. Recently, however, a class of compounds has been defined that are structurally related to the antibiotic tetracyclines, but which have had their antibiotic activity substantially or completely expunged by chemical modification. The modifications that may and may not be made to the basic tetracycline structure have been reviewed by Mitscher (1978). According to Mitscher, modification at positions 5–9 of the tetracycline ring system can be made without causing the complete loss of antibiotic properties.

However, changes to the basic structure of the ring system, or replacement of substituents at positions 1–4 or 10–12, generally lead to synthetic tetracyclines with substantially less, or essentially no, antibacterial activity. For example, 4-de(dimethylamino)tetracycline is commonly considered to be a non-antibacterial tetracycline. These compounds, known as chemically-modified tetracyclines (CMTs) have been found to possess a number of interesting properties, such as the inhibition of excessive collagenolytic activity both in vitro and in vivo. See, for example, Golub et al. (1991).

More recently, it has been established that tetracyclines, which are rapidly absorbed and have a prolonged plasma half-life, exert biological effects independent of their antimicrobial activity (Golub et al. 1991, Golub et al. 1992, Uitto et al. 1994). Such effects include inhibition of some but not all matrix metalloproteinases. Specific activity has been shown with respect to collagenases (MMP-1; MMP-8; MMP-13) and gelatinases (MMP-2; MMP-9), as well as prevention of pathologic tissue destruction (Golub et al. 1991). However, Applicants are not aware of any evidence in the prior art disclosing or suggesting that tetracycline compounds could be of any use in inhibiting MT-MMP activity, either in normal systems or in systems characterized by abnormal or excessive MT-MMP activity.

Recent studies have suggested that, in some systems, certain tetracyclines and inhibitors of metalloproteinases can inhibit tumor progression (DeClerck et al. 1994) or angiogenesis (WIPO publication WO 92/12717; Maragoudakis et al. 1994). Zucker et al. (1985) showed that minocycline can inhibit melanoma cell activity in vitro. Some tetracyclines may exhibit cytostatic effects against some tumors (Kroon et al. 1984; van den Bogert et al. 1986). Pro-gelatinase A (MMP-2) has been reported to be associated with tumor spread (Yu et al. 1997). 6-demethyl-6-deoxy-4-de(dimethylamino)tetracycline (CMT-3) has been shown to experimentally suppress prostate and melanoma tumor growth and metastasis in vivo (Lokeshwar et al. 1998; Seftor et al. 1998).

While tetracycline antibiotics are generally effective for treating infection, the use of these compounds can lead to undesirable side effects. For example, the long term administration of antibiotic tetracyclines can reduce or eliminate healthy microbial flora, such as intestinal flora, and can lead to the production of antibiotic resistant organisms or the overgrowth of yeast and fungi. Accordingly, chemically-modified tetracyclines, in which the antimicrobial activity is attenuated or deleted, can be preferred for use in applications in which anti-collagenolytic activity is indicated.

In view of the above considerations, it is clear that there is a need to supplement existing methods of inhibiting proteinase-mediated physiological and structural changes in biological systems, especially as therapeutic interventions in disease processes. It is also apparent that there is a need for advanced and precise inhibitors of MT-MMP activity in diagnostic and therapeutic applications, especially in respect of those medical conditions that are characterized by excessive MT-MMP activity. In particular, it is desirable to identify new and selective MT-MMP inhibitors with relatively high activity, i.e., being active at doses that are substantially free of harmful side effects.

Accordingly, it is one of the purposes of this invention to overcome the above limitations in modulation or control of proteinase activity, by providing a compound and method for inhibiting membrane-type matrix metalloproteinase, and inhibiting deleterious effects of excessive activity of the enzyme in biological systems. In particular, it is a one of the purposes of the invention to provide new and selective MT-MMP inhibitors that are active at doses that are substantially free of harmful side effects.

SUMMARY OF THE INVENTION

It has now been discovered that these and other objectives can be achieved by the present invention, which provides a method for inhibiting the activity of membrane-type matrix metalloproteinase in a biological system by providing a chemically modified tetracycline to the system in an amount that is effective to achieve the specified result.

In one embodiment, the invention is a method of inhibiting membrane-type matrix metalloproteinase activity in a biological system, comprising delivering to the system in need thereof an MT-MMP-inhibitory amount of a tetracycline compound.

The tetracycline compound is preferably administered in an amount that has substantially no antimicrobial activity. Preferred tetracycline compounds include, for example, 6-demethyl-6-deoxy-4-dedimethylaminotetracyclne (CMT-3) or 6-α-deoxy-5-hydroxy-4-de(dimethylamino) tetracycline (CMT-8).

The biological system can have or be characterized by excessive MT-MMP activity, wherein the method comprises administering to the system an amount of the tetracycline compound sufficient to inhibit the excessive MT-MMP activity.

The biological system can comprise cultured mammalian cells, such as tumor cells, osteoclasts, or fibroblasts. The biological system can be a mammal, such as a mammal that has a condition characterized by excessive MT-MMP activity. Thus the method can be used to treat a mammal that has a cancer, such as a carcinoma, fibrosarcoma, or osteosarcoma. The method can also be used if the mammal has a condition characterized by excessive osteoclast activity.

In an alternative embodiment, the invention is a method of inhibiting MT-MMP activity in a mammal, comprising administering to the mammal an amount of a tetracycline compound sufficient to inhibit MT-MMP activity.

The tetracycline compound is preferably administered in an amount that has substantially no antimicrobial activity. Preferred tetracycline compounds include, for example, 6-demethyl-6-deoxy-4-dedimethylaminotetracycline (CMT-3) or 6-α-deoxy-5-hydroxy-4-de(dimethylamino) tetracycline (CMT-8).

In this method, if the mammal has a condition characterized by excessive MT-MMP activity, the method comprises administering to the mammal an amount of the tetracycline compound sufficient to inhibit excessive MT-MMP activity. The method is useful in cases in which the mammal has a cancer, such as a carcinoma, fibrosarcoma, or osteosarcoma, or a condition characterized by excessive osteoclast activity.

In another embodiment, the invention is a method of inhibiting the invasive potential of carcinoma cells, fibrosarcoma cells, or osteosarcoma cells, comprising contacting the cells with an invasion-inhibitory amount of a tetracycline compound. Preferred tetracycline compounds include, for example, 6-demethyl-6-deoxy-4-de(dimethylamino) tetracycline (CMT-3) or 6-α-deoxy-5-hydroxy-4-de (dimethylamino)tetracycline (CMT-8). More preferably in this embodiment, the method comprises contacting the cancer cells with an amount of CMT-3 or CMT-8 that is sufficient to inhibit membrane-type matrix metalloproteinase activity of the cells.

These and other advantages of the present invention will be appreciated from the detailed description and examples set forth hereinbelow. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawings, wherein:

FIG. 4A is a bar chart showing dose-dependent inhibition of MMP-2 expression by cultured MG-63 osteosarcoma cells.

FIG. 4B is a bar chart showing dose-dependent inhibition of MMP-2 activation in cultured MG-63 osteosarcoma cells.

FIG. 5A is a bar chart showing CMT-3- and CMT-8-mediated inhibition of Matrigel invasion by HT1080 fibrosarcoma cells.

FIG. 5B is a bar chart showing CMT-3 and CMT-8-mediated inhibition of Transwell migration by HT1080 fibrosarcoma cells.

DETAILED DESCRIPTION OF THE PREFERRED EMBODIMENTS

Figure 1:
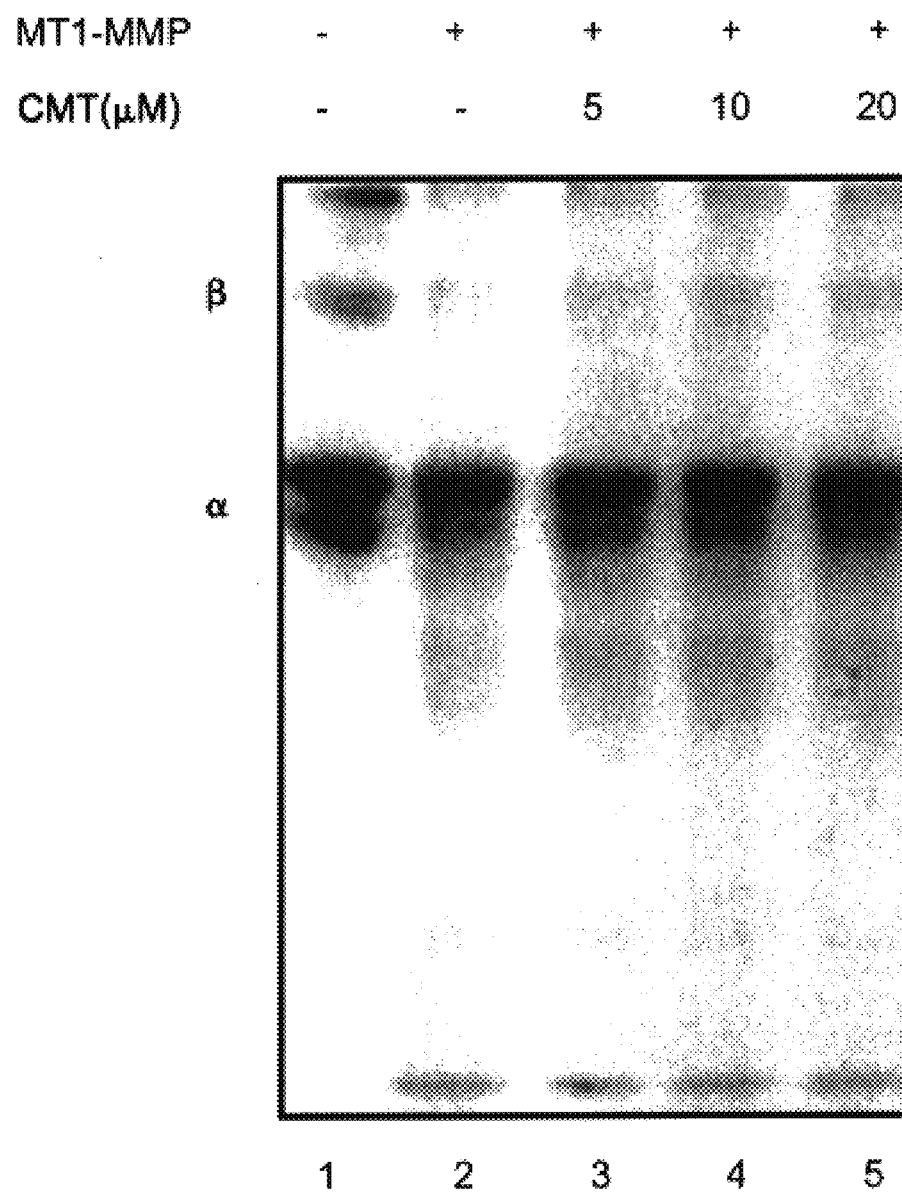
FIG. 1 is a graphical illustration of an autoradiographic analysis of CMT-3-mediated inhibition of gelatinolytic activity exhibited by a membrane fraction of MT1-MMP-transfected COS-1 cells.

In one embodiment, the present invention is directed to a method for inhibiting cancer growth, including processes of cellular proliferation, invasiveness, and metastasis in biological systems. The method includes the use of a tetracycline compound as an inhibitor of cancer growth. Preferably, the method is employed to inhibit or reduce cancer cell proliferation, invasiveness, metastasis, or tumor incidence in living animals, such as mammals. The method is also readily adaptable for use in assay systems, e.g., assaying cancer cell growth and properties thereof The tetracycline compound used in the method of the invention may be any tetracycline compound, from those that have potent antibiotic activity to those lacking any substantial antimicrobial activity. However, it is preferred that the tetracycline compound be administered in an amount that has substantially no antimicrobial activity, but that is effective for inhibiting the activity of an MT-MMP, preferably inhibiting a pathological or excessive activity of MT-MMP. The method can, therefore, take advantage of tetracycline compounds that have been chemically modified to reduce or eliminate their antimicrobial properties.

Such compounds include, for example, those that lack the dimethylamino group at position 4 of the tetracycline ring structure, e.g., 4-de(dimethylamino)tetracycline (CMT-1), 6-demethyl-6-deoxy-4-de(dimethylamino)tetracycline (CMT-3), 7-chloro-4-de(dimethylamino)tetracycline (CMT-4), 4-hydroxy-4-de(dimethylamino)tetracycline (CMT-6), 4-de(dimethylamino)-12α-deoxytetracycline (CMT-7), 6-deoxy-5α-hydroxy-4-de(dimethylamino)tetracycline (CMT-8), 4-dedimethylamino-12α-deoxyanhydrotetracycline (CMT-9), 7-dimethylamino-6-demethyl-6-deoxy-4-de (dimethylamino)tetracycline (CMT-10), 4-de(dimethylamino)-5-oxytetracycline, 5 α,6-anhydro-4-hydroxy-4-de(dimethylamino) tetracycline, 4-de(dimethylamino)11-hydroxy- 12α-deoxytetracycline, 12α-deoxy-4-deoxy-4-de(dimethylamino)tetracycline, and 12α,4αanhydro-4-de(dimethylarnino)tetracycline. Further examples of tetracyclines modified for reduced antimicrobial activity include 6-α-benzylthiomethylenetetracycline, the mono-N-alkylated amide of tetracycline, 6-fluoro-6-demethyltetracycline, 11α-chlorotetracycline, tetracyclinonitrile (CMT-2), and tetracycline pyrazole (CMT-5).

The preferred tetracycline compounds include:

4-de(dimethylamino)tetracycline (CMT-1), tetracyclinonitrile (CMT-2)

6-demethyl-6-deoxy-4-de(dimethylamino)tetracycline (CMT-3), 4-de(dimethylamino)-7-chlorotetracycline (CMT-4), tetracycline pyrazole (CMT-5), 4-hydroxy-4-de(dimethylamino)tetracycline (CMT-6), 4-de(dimethylamino)-12α-deoxytetracycline (CMT-7), 6-deoxy-5α-hydroxy-4-de(dimethylamino)tetracycline (CMT-8), 4-dedimethylamino-12α-deoxyanhydrotetracycline (CMT-9), and 7-dimethylamino-6-demethyl-6-deoxy-4-de(dimethylamino)tetracycline (CMT-10), Particularly preferred modified tetracyclines include CMT-1, CMT-3, CMT-7, and CMT-8. Highly preferred modified tetracycline compounds include CMT-3 and CMT-8. Combinations of these compounds, as well as combinations with other tetracyclines and/or pharmaceutical compounds can be employed.

The use of such chemically-modified tetracyclines (CMTs) is preferred in the present invention since they can be used at higher levels than antimicrobial tetracyclines, while avoiding the disadvantages associated with antimicrobial activity as described elsewhere herein. However, sub-antimicrobial doses of typically antibacterial tetracyclines (e.g., doxycycline) can also be given according to the invention.

Preferred compounds having substantial antimicrobial activity include, for example, tetracycline, doxycycline, and minocycline and other well known tetracycline antibiotics, especially those already approved for use in humans.

These compounds exhibit their MT-MMP-inhibitory properties at concentrations that lead to relatively few, and in some cases are substantially free of side effects. For example, the useful concentrations of preferred chemically-modified tetracyclines do not present any significant antimicrobial activity. Such non-antimicrobial tetracycline compounds are useful for extended treatment protocols, where other compounds would exhibit undesirable side-effects.

The tetracycline compounds useful according to the invention possess a desirable but unusual combination of physicochemical properties, including activity, bioavailability, solubility, and reduction of side effects. These properties render the compounds particularly desirable for the inhibition of MT-MMP activity in mammals. In addition, it is believed that the properties of hydrophilicity and hydrophobicity are well balanced in these compounds, enhancing their utility both in vitro and especially in vivo, while other compounds lacking such balance are of substantially less utility. Specifically, the compounds have an appropriate degree of solubility in aqueous media to permit absorption and bioavailability in the body, while also having a degree of solubility in lipids to permit traversal of the cell membrane to a putative site of action. The compounds are maximally effective if they can be delivered to the site or region of the MT-MMP activity, and additional advantage can be obtained if the ability of the compound to localize to expressed MT-MMP is maximized.

In the treatment of certain localized conditions, the degree of hydrophilicity of the non-antimicrobial tetracycline compound can be of lesser importance. Such compounds as tetracyclinonitrile (CMT-2) and 4-hydroxy-4-de(dimethylamino)tetracycline (CMT-6), which have low solubility in aqueous systems, can be used in direct or topical treatment of skin conditions characterized by MT-MMP, or by implantation into the brain to topically treat brain conditions. Animal experiments, in which adult rats are orally gavaged with these two CMTs, have shown no detectable blood levels of these compounds, indicating a lack of systemic absorption and/or extraordinarily rapid excretion.

This embodiment of the invention has been developed based on the unexpected observation by Applicants that certain tetracycline compounds, chemically modified to eliminate substantially all antimicrobial activity, are effective to inhibit the activity of MT-MMP and to reduce deleterious or injurious effects associated with MT-MMP activity. Of these, one especially preferred CMT, i.e., 6-demethyl-6-deoxy-4de(dimethylamino)tetracycline (also referred to as "CMT-3"), appears to possess an excellent balance of properties, in that it is shown to possess unusually strong activity in inhibiting MT-MMP activity. Another advantage of CMT-3 is that it has an unexpectedly long serum half-life (approximately 28 hr). Therefore, CMT-3 may only require periodic administration, e.g., once or twice per week.

In another embodiment, the method of the invention is effective to inhibit the enzymatic activity of membrane-type matrix metalloproteinase associated with medical conditions in mammals. The MT-MMP activity capable of inhibition may derive from MT-MMP expression by the diseased tissue or from normal tissue. In particular, the MT-MMP activity may be derived from such normal tissues as epithelial tissue or stromal tissue. More preferably, the method can be used to inhibit excessive MT-MMP activity associated with cancerous tumors. This inhibition of observed gelatinolytic activity may be due to inhibition of MT-MMP activity, down-regulation of MT-MMP expression, or some other interference with the physiology associated with this enzyme, such as inhibition of activation of a precursor form of the enzyme.

Applicants have discovered that the chemically modified tetracyclines decrease the level of activity of MT-MMP expressed by several types of human cancer cell lines, including carcinoma, fibrosarcoma, and osteosarcoma cells. Applicants believe that this observation carries significant therapeutic implications for cancer treatment. Applicants also understand that these CMTs and other chemically and functionally related compounds would be useful for inhibiting the consequences of other diseases characterized by excessive MT-MMP expression or activity.

The use of the method of the invention in the inhibition of cancer cell growth or proliferation can occur with less cytotoxicity to normal cells or tissues than is found with conventional cytotoxic cancer therapeutics, preferably without substantial cytotoxicity to normal cells or tissues. For example, it has been unexpectedly observed that a tetracycline, e.g., CMT-3, can inhibit MT-MMP activity in cancer cells while producing little or substantially no cytotoxicity in normal cells.

The data presented in the examples below, reveal that cancer cells treated with these compounds results in a decrease in extracellular gelatinolytic activity, a corresponding dose-dependent decrease in the cells' in vitro invasive potential, and a decrease in the cells' metastatic ability in vivo. Moreover, the compounds can induce killing of tumor cells, and can do so while being substantially non-cytotoxic to normal tissues. Accordingly, these chemically-modified tetracyclines can be used to suppress the formation and magnitude of metastases associated with certain cancers, used as an adjunct to other treatment regimens, and lead to greater efficacy in the treatment of metastatic cancers.

The method of the invention can be used in any biological system, whether in vitro, ex vivo, or in vivo. In vitro biological systems typically include cultured cells or tissues, but may involve isolated or purified organelles or cellular components. For example, MT-MMP is expressed as a membrane-bound protein, and a membrane fraction containing the enzyme can be isolated and tested in vitro. Diagnostic tests, such as to measure an index of MT-MMP activity, are typically performed in vitro. Ex vivo biological systems typically include organ systems removed from a living animal. In vivo uses are limited to biological systems that are living animals, and such uses typically include therapeutic or pharmaceutical interventions. Thus, embodiments of the invention in which a tetracycline compound is administered to a mammal are representative of in vivo methods.

The conditions treatable by means of the present invention occur in mammals. Mammals include, for example, humans, as well as pet animals such as dogs and cats, laboratory animals such as rats and mice, and farm animals such as horses and cows.

The method of the invention is useful to treat medical conditions characterized by MT-MMP activity. In particular, the invention is useful in the treatment (e.g., palliation, amelioration) of medical conditions characterized by excessive or pathological levels of MT-MMP activity. Such conditions include, but are not limited to conditions characterized by increased levels of osteoclast cell activity, e.g., different types of arthritis, osteoporosis and other conditions characterized by bone resorption. Various inflammatory conditions are also characterized by excessive MT-MMP activity, and the method can be used to inhibit MT-MMP activity in those in mammals subject to or susceptible to such conditions.

Excessive MT-MMP activity is also observed in association with cancers. Accordingly, other conditions susceptible to treatment according to the invention include cancerous conditions, e.g., tumors or neoplasms. Neoplastic conditions treatable by the present invention include all solid tumors, i.e., carcinomas and sarcomas. Carcinomas include those malignant neoplasms derived from epithelial cells which tend to infiltrate (invade) the surrounding tissues and give rise to metastases. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Sarcomas include, for example, osteosarcomas and fibrosarcomas.

The invention is particularly illustrated herein in reference to treatment of certain types of experimentally defined cancers. In these illustrative treatments, standard state-of-the-art in vitro and in vivo models have been used. These methods can be used to identify agents that can be expected to be efficacious in in vivo treatment regimens, without regard to whether the condition to be treated is cancerous. Thus, it will be understood that the method of the invention is not limited to the treatment of these tumor types, but extends to any medical condition affecting any organ system, such as inflammatory diseases, provided that the condition characteristically is associated with MT-MMP activity, especially excessive MT-MMP activity.

The observed inhibition of MT-MMP activity effect occurs over a wide range of concentrations, including at concentrations that are extraordinarily low. The amount of the tetracycline compound used according to the invention is an amount that is effectively inhibitory of MT-MMP activity. An amount of a tetracycline compound is effectively inhibitory to MT-MMP activity if it significantly reduces MT-MMP activity in a biological system.

Preferably, the tetracycline compound is provided in an amount that has little or no antimicrobial activity. A tetracycline compound is not effectively antimicrobial if it does not significantly prevent the growth of microbes. Accordingly, the method can beneficially employ a tetracycline compound that has been modified chemically to reduce or eliminate its antimicrobial properties. The use of such chemically-modified tetracyclines is preferred in the present invention since they can be used at higher levels than antimicrobial tetracyclines, while avoiding certain disadvantages, such as the indiscriminate killing of beneficial microbes, and the emergence of resistant microbes, which often accompanies the use of antimicrobial or antibacterial amounts of such compounds over prolonged periods of time.

The tetracycline compounds useful according to the method of the invention appear to exhibit their beneficial effect in a dose-dependent manner. Thus, within broad limits, administration of larger quantities of a tetracycline compound has been observed to inhibit MT-MMP activity to a greater degree than does administration of a smaller amount. Moreover, efficacy has been observed at dosages below the level at which toxicity is seen in normal cells or at the organismal level. Accordingly, one of the advantages of the invention is that the debilitating side effects that may be attendant upon conventional therapeutic regimens are reduced, and preferably avoided.

The maximal dosage for a subject is the highest dosage that does not cause undesirable or intolerable side effects. For example, the tetracycline compound(s) can be administered in an amount of from about 0.1 mg/kg/day to about 30 mg/kg/day, and preferably from about 1 mg/kg/day to about 18 mg/kg/day. For the purpose of the present invention, side effects may include clinically significant antimicrobial or antibacterial activity, as well as toxic effects. For example, a dose in excess of about 50 mg/kg/day would likely produce side effects in most mammals, including humans. In any event, the practitioner is guided by skill and knowledge in the field, and the present invention includes, without limitation, dosages that are effective to achieve the described phenomena.

The invention can also be practiced by including with the tetracycline compound one or more other therapeutic agents, such as any conventional inhibitor of other metalloproteinases. The combination of the tetracycline compound with such other agents can potentiate the therapeutic protocol. Numerous therapeutic protocols will present themselves in the mind of the skilled practitioner as being capable of incorporation into the method of the invention. Any chemotherapeutic agent can be used, including alkylating agents, antimetabolites, hormones, radioisotopes, non-steroidal anti-inflammatory drugs (NSAIDs), enzyme substrates or inhibitors, receptor agonists and antagonists, as well as natural products.

The preferred pharmaceutical composition for use in the method of the invention includes a combination of the tetracycline compound in a suitable pharmaceutical carrier (vehicle) or excipient as understood by practitioners in the art.

Enteral administration is a preferred route of delivery of the tetracycline, and compositions including the tetracycline compound with appropriate diluents, carriers, and the like are readily formulated. Liquid or solid (e.g., tablets, gelatin capsules) formulations can be employed. It is among the advantages of the invention that, in many situations, the tetracycline compound can be delivered orally, as opposed to parenteral delivery (e.g., injection, infusion) which is typically required with conventional chemotherapeutic agents.

Parenteral use (e.g., intravenous, intramuscular, subcutaneous injection) is also contemplated, and formulations using conventional diluents, carriers, etc., such as are known in the art can be employed to deliver the compound.

Alternatively, delivery of the tetracycline compound can include topical application. Compositions deemed to be suited for such topical use include as gels, salves, lotions, ointments and the like. In the case of tumors having foci inside the body, e.g., brain tumors, the tetracycline compound can be delivered via a slow-release delivery vehicle, e.g., a polymeric material, surgically implanted at or near the lesion situs.

The following examples are provided to assist in a further understanding of the invention. The particular materials and conditions employed are intended to be further illustrative of the invention and are not limiting upon the reasonable scope thereof.

EXAMPLE 1A

Preparation of MT1-MMP- or pro-MMP-2-Transfected Cells $MT_1$-MMP- and pro-gelatinase A-transfected COS-1 cells were prepared in general accordance with the protocol of Cao et al. (1996). Specifically, COS-1 cells were cultured in DMEM (Life Technologies) containing 10% fetal bovine serum (Atlanta Biologicals) and 2 mM glutamine under 5% $CO_2$/95% air atmosphere. On the day of transfection with either pro-gelatinase A or $MT_1$-MMP, the COS-1 cells were washed with phosphate-buffered saline, pH 7.4 (PBS), followed by the addition of DMEM containing 10% NUSERUM®, 300 mg/mL DEAE-dextran, 100 mM chloroquine, and 1.25 mg/mL DNA. Plasmids containing cDNAs of $MT_1$-MMP or pro-gelatinase A were used for transfection.

The cells were then incubated for 4 hr at 37° C. in a 5% $CO_2$ atmosphere. Then the cells were washed once with DMEM and incubated for 2 min in 10% DMSO in $Ca^{2+}$/$Mg^{2+}$-free PBS at room temperature, and washed twice with PBS. Finally, the cells were incubated for 1 day in DMEM containing 10% fetal bovine serum.

EXAMPLE 1B

Preparation of Cell Membrane Fractions of MT1-MMP-Transfected Cells

Confluent $MT_1$-MMP-transfected COS-1 cells ($2 \times 10^7$ cells) were harvested following treatment with trypsin-EDTA and washed thoroughly. Cells were suspended in 25 mM sucrose, 5 mM $MgCl_2$ in Tris base, pH 7.4, and then subjected to nitrogen ($N_2$) cavitation at 1000 p.s.i. for 30 min at 4° C. Whole cells and nuclei were removed by centrifugation at 770×g for 10 min, and the postnuclear supernatant was centrifuged at 6,000×g for 15 min to remove heavy organelles. The supernatant was centrifuged at 100,000×g for 60 min, and the cell membrane fraction, comprising plasma membranes, Golgi, and ribosomes, was recovered in the pellet. The 100,000×g supernatant was designated as cytosol.

EXAMPLE 2

Direct Digestion of Gelatin by $MT_1$-MMP is Inhibited by CMT-3

Radiolabeled ($^3$H) collagen type I was denatured, to unravel the triple helix to produce [$^3$H-methyl]-gelatin. When separated by SDS-PAGE, and examined by autoradiography, the denatured collagen yields three bands: α (~100 kDa), β (~200 kDa), and γ (~300 kDa), corresponding to the various components of the collagen in the sample. The tritiated gelatin substrate was incubated with a membrane fraction obtained by $MT_1$-MMP-transfected COS-1 cells as described above. The gelatinolytic activity was calculated as % lysis of the α, β, and γ intact gelatin components assessed by laser densitometer scanning of the fluorogram.

$MT_1$-MMP exhibited degradative activity using gelatin as substrate, and CMT-3 at 5, 10, and 20 μM inhibited this gelatinolytic activity by 16.3%, 35%, and 32% respectively as shown in FIG. 1:

| | |
|---|---|
| Lane 1 | [$^3$H-methyl] gelatin, α, β, and γ chains were intact; |
| Lane 2 | [$^3$H-methyl] gelatin and $MT_1$-MMP incubated for 18 hr at 37° C.; and |
| Lanes 3–5 | CMT-3 was added to the incubation mixture of [$^3$H-methyl] gelatin and $MT_1$-MMP at final concentrations of 5 μM (Lane 3), 10 μM (Lane 4), and 20 μM (Lane 5). |

The MT-MMP caused a characteristic loss of each of the 100 kDa, 200 kDa, and 300 kDa bands, with the formation of low molecular weight (<100 kDa) bands, corresponding to gelatin digestion products. However, when the incubation was performed in the presence of CMT-3 (5 μM to 20 μM), a dose-dependent decrease in the low molecular weight bands was seen with a corresponding increase in the residual intact gelatin bands. These data show that CMT-3 inhibits the characteristic ability of MT-MMP to directly degrade gelatin.

EXAMPLE 3

Activation of Gelatinase A by MT1-MMP is Inhibited by CMT-3

Recombinant pro-gelatinase A (72 kDa type IV gelatinase) can be activated to form 62 kDa active gelatinase by MT-MMP-containing plasma membrane fractions. To examine the ability of a tetracycline compound to inhibit this gelatinase activating property of MT-MMP, membrane fractions obtained according to Example 1B were incubated with recombinant human pro-gelatinase A for 18 h at 37° C. with or without CMT-3, and examined by zymography to evaluate enzyme activation.

Specifically, pro-MMP-2 was obtained from the culture-conditioned medium from MMP-2-transfected COS-1 cells. The $MT_1$-MMP membrane fraction preparation exhibited pro-MMP-2 activating activity by inducing the characteristic molecular weight shift from 72 kDa (pro-MMP-2) to 62 kDa (active MMP-2) as measured by gelatin zymography, generally in accordance with the following conventional protocol:

Conditioned media were collected from the cultures that had been treated with CMT-3 for 2 days. Media were then incubated with SDS-gel electrophoresis sample buffer for 30 min at room temperature, and then analyzed by gel electrophoresis on SDS-polyacrylamide gel (10%) containing gelatin (1 mg/mL; Novex, Inc.). Following electrophoresis, the gels were washed twice with 0.25% TRITON®X-100 for 30 min each (to renature the gelatinase), and incubated for 18–24 hr at 37° C. in a Tris-HCl buffer, pH 7.4 (see, e.g., Lokeshwar 1993). After incubation, the gels were briefly rinsed in distilled water and stained with 0.25% Coomassie brilliant blue R250. The location of gelatinase activity in the gels is visible as a colorless area on an otherwise uniform blue background, indicative of digested gelatin. Note that under zyrnography, both the 72 kDa and the 62 kDa forms of gelatinase exhibit gelatinolytic activity, thus permitting one to distinguish these forms on the basis of their differences in molecular weight.

Figure 2:
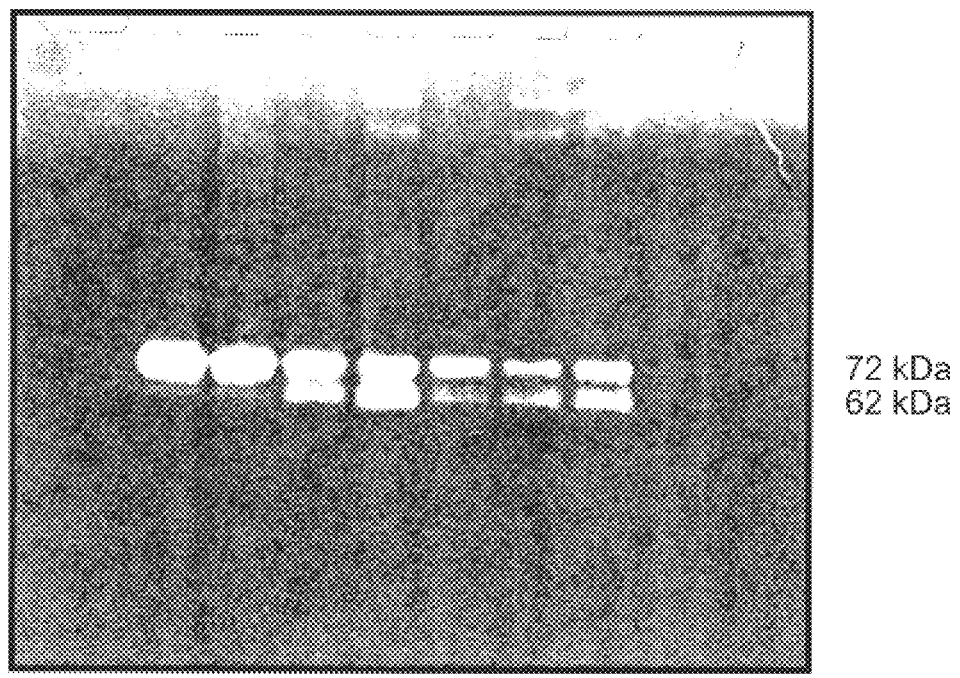
FIG. 2 is a graphical illustration of a zymographic analysis CMT-3-mediated inhibition of gelatinase activation by recombinant MT1-MMP.

The results of this experiment are illustrated in the zymogram shown as FIG. 2:

| | |
|---|---|
| Lane 1 | Pro-gelatinase A |
| Lane 2 | Pro-gelatinase A + membrane fraction control (membrane fraction from COS-1 cells transfected with vector absent the $MT_1$-MMP gene); |
| Lanes 3–4 | Pro-gelatinase A + $MT_1$-MMP (duplicates); |
| Lane 5 | Pro-gelatinase A + $MT_1$-MMP + 50 $\mu$M CMT-3; |
| Lane 6 | Pro-gelatinase A + $MT_1$-MMP + 20 $\mu$M CMT-3; and |
| Lane 7 | Pro-gelatinase A + $MT_1$-MMP + 10 $\mu$M CMT-3. |

This experiment demonstrated that recombinant pro-gelatinase A can be activated to form 62 kDa active gelatinase by plasma membrane fractions of $MT_1$-MMP-transfected cells. Moreover, as shown in FIG. 2, CMT-3 at final concentrations of 10, 20, and 50 $\mu$M inhibited the $MT_1$-MMP-induced activation of pro-gelatinase A assessed by gelatin zymography in a dose-dependent manner. Thus, CMT-3 blocked $MT_1$-MMP-mediated activation of pro-gelatinase A.

EXAMPLE 4A

Figure 3A:
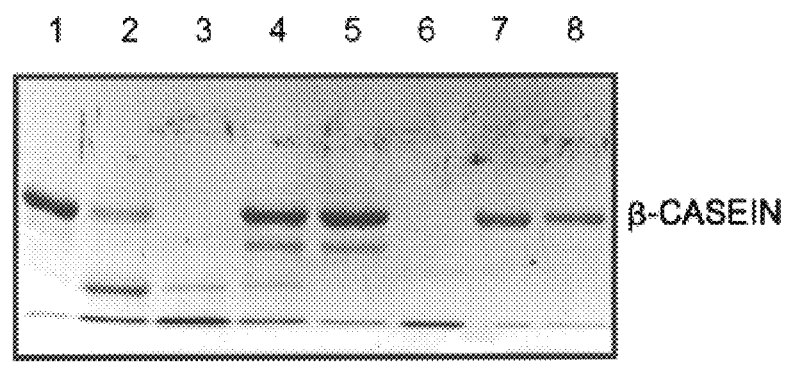
FIG. 3A is a graphical illustration of a zymographic analysis of CMT-3-mediated inhibition of caseinolytic activity of recombinant MT1-MMP.

In FIG. 3A, the proteolytic activity of $MT_1$-MMP and its inhibition by a tetracycline compound was assessed using casein zymography:

| | |
|---|---|
| Lane 1 | 21 kDa intact β-casein substrate (52 $\mu$M); |
| Lane 2 | degraded β-casein, by 50 ng of $MT_1$-MMP, into a smaller molecular weight fragments; |
| Lanes 3–5 | progressive inhibition of caseinolytic activity by increasing (0.5, 1.5, and 3.0 $\mu$M, respectively) concentrations of CMT-3; and |
| Lanes 6–8 | $MT_1$-MMP incubated with β-casein substrate with proteinase inhibitors: 0.5 mM PMSF, 2 mM EDTA, and TIMP-2 (1:1 molar ratio), respectively. |

Consistent with $MT_1$-MMP activity against casein reflecting metalloproteinase and not serine proteinase activity, PMSF did not inhibit caseinolytic activity (Lane 6) whereas EDTA (Lane 7) and TIMP-2 (Lane 8) did inhibit the caseinolytic activity.

EXAMPLE 4B

The proteolytic activity of $MT_1$-MMP was assessed using gelatinase A zymography. Pure recombinant pro-MMP-2 (72 kDa gelatinase or pro-gelatinase A) and $MT_1$-MMP were co-incubated in the presence or absence of CMT-3 (0.5–3.0 $\mu$M). After incubation, the enzyme mixture was examined by SDS-PAGE and the protein (enzyme) bands were stained with Coomassie brilliant blue. The results are illustrated in FIG. 3B:

| | |
|---|---|
| Lane 1 | Pro-gelatinase A is shown as a single band (72 kDa); |
| Lane 2 | the conversion of pro-gelatinase A (72 kDa) to a smaller molecular weight active gelatinase A (62 kDa) mediated by incubation with 50 ng recombinant $MT_1$-MMP; |
| Lanes 3–6 | the gelatinase A activated with $MT_1$-MMP was incubated with 0.5, 1.0, 1.5 and 3.0 $\mu$M CMT-3, respectively; and |
| Lane 7 | molecular weight standard. |

Figure 3B:
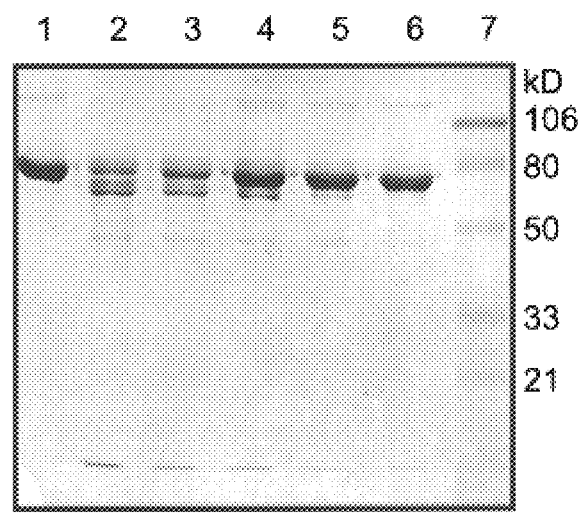
FIG. 3B is a graphical illustration of a zymographic analysis CMT-3-mediated inhibition of pro-gelatinase A activation by recombinant MT1-MMP.

FIG. 3B clearly shows progressive inhibition of the conversion of pro-gelatinase A to active gelatinase A (approximately 10 kDa lower molecular weight than the precursor) in a dose-response fashion. Note in particular that 3.0 $\mu$M CMT-3 (Lane 6) essentially completely inhibits the formation of the smaller molecular weight species of gelatinase A by $MT_1$-MMP.

EXAMPLE 5

MG-63 cells, an osteosarcoma cell line, were grown in culture and treated with 40 $\mu$g/mL concanavalin A to induce $MT_1$-MMP-dependent activation of pro-MMP-2. Culture-conditioned medium was collected, as a source of pro-MMP-2, and was incubated in the presence of the membrane fraction of COS-1 cells transfected to express $MT_1$-MMP. The incubated medium showed gelatin-degrading activity by zymographic analysis, which was inhibited by 0.5 $\mu$M to 3.5 $\mu$M CMT-3, in a dose-dependent manner (FIG. 4A). Moreover, the percent of activated MMP-2 in the total expressed MMP-2 was decreased in a dose-dependent fashion (FIG. 4B). Note in FIG. 3B, that at CMT-3 concentrations of 3.0 $\mu$M and 3.5 $\mu$M, no active MMP-2 was detected. Thus, CMT-3 not only inhibited expression of gelatinase expressed by the osteosarcoma cells, it also inhibited activation of the expressed gelatinase.

EXAMPLE 6A

Inhibition of Matrigel Invasion of HT-1080 Fibrosarcoma Cell by CMTs.

HT-1080 cells were allowed to invade through Matrigel (Collaborative Research, Bedford, Mass.) for 24 hr in medium containing 10% serum. CMT-3 or CMT-8 were added to the medium to assess their ability to inhibit invasivity of the cells. CMT-3 was tested at final concentrations of 1 $\mu$M or 10 $\mu$M; CMT-8 was tested twice at a final concentration of 50 $\mu$M. The invading cells were counted, and the relative numbers of cells were expressed as means of triplicate measurements. The results are presented in FIG. 5A.

EXAMPLE 6B

HT-1080 cells were allowed to migrate in the presence of medium containing 10% serum for 18 hr in Transwell chambers (Costar, Cambridge, Mass.). The concentrations of CMT-3 and CMT-8 are indicated, and noteworthy a clear inhibition of HT-1080 fibrosarcoma cell migration is observed already at 0.5 $\mu$M CMT-3 and CMT-8 concentrations. The results of this study are summarized in FIG. 5B, showing the relative number of cells having traversed to the undersurface of Transwell chambers. The data are expressed as means of triplicate measurements.

In Examples 6A and 6B, CMT-3 and CMT-8 were found to suppress the invasion (FIG. 5A) and migration (FIG. 5B) of HT-1080 fibrosarcoma cells starting at 1–10 $\mu$M and reaching maximal inhibition at 50 $\mu$M. CMT-3 was slightly more effective in comparison to CMT-8 in prevention of invasion (FIG. 5A). Effective inhibition of HT-1080 cell migration was seen at concentrations as low as 0.5 $\mu$M CMT-3 and CMT-8 (FIG. 5B). The concentrations required to inhibit 50% ($IC_{50}$) $MT_1$-MMP activity and $MT_1$-MMP-dependent activation of proMMP-2 as well as the in vitro invasion and migration of HT-1080 cells were 1–3 $\mu$M. CMT-3 and CMT-8 did not block cell surface integrins, did not prevent initial attachment and spreading of studied cell lines on extracellular matrix or Matrigel substrate, and was not cytotoxic to the cells under the conditions used (data not shown).

Therapeutically attainable CMT concentrations (<2 $\mu$M) directly inhibit the $MT_1$-MMP activity, the activation of proMMP-2 by $MT_1$-MMP and prevent in vitro invasion and migration of malignant human cells, such as HT-1080 fibrosarcoma cell line which are capable of expressing both $MT_1$-MMP and MMP-2. Thus CMTs can be regarded as drugs with MMP-inhibitory and anti-invasive properties, and they could be considered not only for the prevention of bone destruction but also for inhibition of soft tissue destruction in the treatment of human inflammatory and malignant diseases.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

The following publications, having been mentioned in the foregoing specification, are incorporated herein by reference for all that they disclose:

Cao J, Rehemtulla A, Bahou W, and Zucker S, "Membrane type matrix metalloproteinase 1 activates progelatinase A without furin cleavage of the N-terminal domain," *J Biol Chem* 271:30174–30180 (1996).

Cao J, Lee H M, Bahou W, and Zucker S, "The propeptide domain of membrane type 1-matrix metalloproteinase (MT1-MMP) is required for progelatinase A activation and binding of TIMP-2," *AACR Annual Meeting,* March 28-April 1, New Orleans, LA (1998).

DeClerck Y A, Shimada H, Taylor S M, and Langley K E, "Matrix metalloproteinases and their inhibitors in tumor progression," *Annals NY Acad Sci* 732:222–232 (1994).

Fridman R, Toth M, Pena D, and Mobashery S, "Activation of progelatinase B (MMP-9) by gelatinase A (MMP-2)," *Cancer Res* 55:2548–2555 (1995).

Golub L M, Ramamurthy N S, McNamara T F, Greenwald R A, and Rifkin B R, "Tetracyclines inhibit connective tissue breakdown: New therapeutic implications for an old family of drugs," *Crit Rev Oral Biol Med* 2(2):297–322 (1991).

Golub L M, Sorsa T, and Suomalainen K, *Curr Opin Dent* 2:80–90 (1992).

Imai K, Ohuchi E, Aoki T, Nomura H, Fujii Y, Sato H, Seiki M, and Okada Y, *Cancer Res* 56:2702–2710 (1996).

Kroon A M, Dontje B H J, Holtrop M, and van den Bogert C, "The mitochondrial genetic system as a target for chemotherapy: tetracyclines as cytostatics," *Cancer Letts* 25(1):33–40 (1984).

Lee A Y, Akers K T, Collier M, Li T, Eisen A Z, and Seltzer J L, "Intracellular activation of gelatinase A (72-kDa type IV collagenase) by normal fibroblasts," *Proc Natl Acad Sci USA* 94(9):4424–4429 (1997).

Lichte A, Kolkenbrock H, and Tschesche H, "The recombinant catalytic domain of membrane-type matrix metalloproteinase-1 ($MT_1$-MMP) induces activation of progelatinase A and progelatinase A complexed with TIMP-2," *FEBS Lett* 397:277–287 (1996).

Lokeshwar B L, Selzer M G, Block N L, and Gunja-Smith Z, "Secretion of matrix metalloproteinases and the inhibitors (TIMPs) by human prostate in explant cultures: Reduced tissue inhibitor of metalloproteinase secretion by malignant tissues," *Cancer Res* 53:4493–4498 (1993).

Lokeshwar B L, Seizer M G, Dudak S M, Block N L, and Golub L M, "Inhibition of tumor growth and metastasis by oral administration of a non-antimicrobial tetracycline analog (CMT-3) and doxycycline in a metastatic prostate cancer model," *Cancer Res* (submitted for publication).

Maragoudakis M E, Peristeris P, Missirlis E, Aletras A, Andriopoulou P, and Haralabopoulos G, *Annals NY Acad Sci* 732:280–293 (1994).

Mitscher L A, *The Chemistry of the Tetracycline Antibiotics,* Ch. 6, Marcel Dekker, New York (1978).

Murphy G, Willenbrock F, Ward R V, Cockett M I, Eaton D, and Docherty A J, *Biochem J* 283:637–641 (1992).

Nagase H, "Matrix metalloproteinases," Chapter 7, pp. 153–204, in *Zinc Metalloproteinases in Health and Disease,* Hooper N M, ed., Taylor and Francis, London (1996).

Ohuchi E, Imai K, Fujii Y, Sato H, Seiki M, and Okada Y, "Membrane type 1 matrix metalloproteinase digests interstitial collagens and other extracellular matrix macromolecules," *J Biol Chem* 272(4):2446–2451 (1997).

Okada Y, Bellocq J-P, Rouyer N, Chenard M-P, Rio M-C, Chambon P, and Basset P, "Membrane-type matrix metalloproteinase (MT-MMP) gene is expressed in stromal cells of human colon, breast, and head and neck carcinomas," *Proc Natl Acad Sci USA* 92:2730–2734 (1995).

Pei D and Weiss S J, *Nature* 371:244–247 (1995).

Sato H, Takino T, Okada Y, Cao J, Shinigawa A, Yamamoto E, and Seiki M, "A matrix metalloproteinase expressed on the surface of invasive tumour cells," *Nature* 370:61–65 (1994).

Sato H, Kinoshita T, Takino T, Nakayama K, and Seiki M, "Activation of a recombinant membrane type 1- matrix metalloproteinase (MT1-MMP) by furin and its interaction with tissue inhibitor of metalloproteinases (TIMP)-2," *FEBS Lett* 393:101–104 (1996).

Sato T, del Carmen Ovejero M, Hou P, Heegaard A M, Kumegawa M, Foged N T, and Delaisse J M, "Identification of the membrane-type matrix metalloproteinase $MT_1$-MMP in osteoclasts," *J Cell Science* 110:589–596 (1997).

Seftor R E B, Seftor E A, DeLarco J E, Kleiner D E, Leferson J, Stetler-Stevenson W G, McNamara T F, Golub L M, and Hendrix M J C, "Chemically-modified tetracyclines inhibit human melanoma cell invasion and metastasis," *Clin Exp Metastasis* 16 (In Press).

Shofuda K, Yasumitsu H, Nishihashi A, Miki K, and Miyazaki K, "Expression of three membrane-type matrix metalloproteinases (MT-MMPs) in rat vascular smooth muscle cells and characterization of MT3-MMPs with and without transmembrane domain," *J Biol Chem* 272(15) 9749–9754 (1997).

Strongin A Y, Collier I, Bannikov G, Marmer B L, Grant G A, and Goldberg G I, "Mechanism of cell surface activation of 72 kDa Type IV collagenase: Isolation of the activated form of the membrane metalloproteinase," *J Biol Chem* 270(10):5331–5338 (1995).

Takino T, Sato H, Yamrnamoto E, and Seiki M, "Cloning of a human gene potentially encoding a novel matrix metalloproteinase having a C-terminal transmembrane domain," *Gene* 155:239–298 (1994).

Uitto V J, Firth J D, Nip L, and Golub L M, *Annals NY Acad Sci* 732:140–151 (1994).

van den Bogert C, Dontje B H J, Holtrop M, Melis T E, Romijn J C, van Dongen J W, and Kroon A M, "Arrest of the proliferation of renal and prostate carcinomas of human origin by inhibition of mitochondrial protein synthesis," *Cancer Res* 46(7):3283–3289 (1986).

Yu A E, Hewitt R E, Connor E W, Stetler-Stevenson W G, "Matrix metalloproteinases, Novel targets for directed cancer therapy," *Clin Pharmacol* 11:229–244 (1997).

Zucker S, Lysick R M, Ramamurthy N S, Golub L M, Wieman J M, and Wilkie D P, "Diversity of plasma membrane proteinases in mouse melanoma cells: Inhibition of collagenolytic activity and cytolytic activity by minocycline," *J Natl Cancer Inst* 75:517–525 (1985).

Zucker S, Conner C, DiMassimo B I, Ende B I, Drews M, Seiki M, and Bahou W F, *J Biol Chem* 270:23730–23738 (1995).

What is claimed is:

1. A method of inhibiting membrane-type matrix metalloproteinase activity in a biological system, comprising administering to the system in need thereof an MT-MMP-inhibitory amount of a tetracycline compound selected from the group consisting of:

4-de(dimethylamino)tetracycline, tetracyclinonitrile, 6-demethyl-6-deoxy-4-de(dimethylamino)tetracycline, 4-de(dimethylamino)-7-chlorotetracycline, 4-hydroxy-4-de(dimethylamino)tetracycline, 4-de(dimethylamino)-12α-deoxytetracycline, 6-α-deoxy-5-hydroxy-4-de(diinethylamino)tetracycline, 4-de(dimethylamino)-12α-deoxyanhydrotetracycline, and 4-de(dimethylamino)minocycline.

2. A method according to claim 1, wherein the tetracycline compound is 6-demethyl-6-deoxy-4-dedimethylaminotetracycline, or 6-α-deoxy-5-hydroxy-4-de(dimethylamino)tetracycline.

3. A method according to claim 1, wherein the biological system has excessive MT-MMP activity, and the method comprises administering to the system an amount of the tetracycline compound sufficient to inhibit the excessive MT-MMP activity.

4. A method according to claim 1, wherein the biological system comprises cultured mammalian cells.

5. A method according to claim 1, wherein the biological system is a mammal.

6. A method according to claim 5, wherein the mammal has a condition characterized by excessive MT-MMP activity.

7. A method according to claim 5, wherein the mammal has a condition characterized by excessive osteoclast activity.

* * * * *